United States Patent
Nagata et al.

[11] Patent Number: 5,616,806
[45] Date of Patent: Apr. 1, 1997

[54] PROCESS FOR PREPARING HIGH-PURITY ANILINE

[75] Inventors: Teruyuki Nagata; Katsuji Watanabe; Yoshitsugu Kono, all of Omuta; Akihiro Tamaki, Yokohama; Takashi Kobayashi, Omuta, all of Japan

[73] Assignee: Mitsui Toatsu Chemicals, Inc., Tokyo, Japan

[21] Appl. No.: 760,771

[22] Filed: Sep. 17, 1991

[30] Foreign Application Priority Data

Sep. 18, 1990 [JP] Japan .................. 2-246281

[51] Int. Cl.$^6$ ............................... C07C 209/22
[52] U.S. Cl. ............................... 564/423
[58] Field of Search .............................. 564/423

[56] References Cited

U.S. PATENT DOCUMENTS

| | | | |
|---|---|---|---|
| 2,292,879 | 8/1942 | Kise | 260/580 |
| 2,823,235 | 2/1958 | Graham et al. | 260/580 |
| 3,265,636 | 8/1966 | Spiegler | 252/447 |
| 3,270,057 | 8/1966 | Cooke et al. | 260/580 |
| 3,328,465 | 6/1967 | Spiegler | 260/580 |
| 3,729,512 | 4/1973 | L'Eplattenier et al. | 260/580 |
| 3,935,264 | 1/1976 | Bhutani | 260/580 |
| 4,212,824 | 7/1980 | Seagraves | 260/580 |
| 4,772,750 | 9/1988 | Habermann | 564/472 |
| 4,990,663 | 2/1991 | Chang et al. | 564/5 |

FOREIGN PATENT DOCUMENTS

| | | |
|---|---|---|
| 0458006 | 11/1991 | European Pat. Off. . |
| 50-15779 | 6/1975 | Japan . |
| 57-167946 | 10/1982 | Japan . |
| 58-4750 | 1/1983 | Japan . |
| 58004750 | 1/1983 | Japan . |
| 62-42956 | 2/1987 | Japan . |
| 62-45567 | 2/1987 | Japan . |

OTHER PUBLICATIONS

Hackh's Chemical Dictionary, 3d. Ed. (1948) p. 686.

*Primary Examiner*—Brian M. Burn
*Attorney, Agent, or Firm*—Millen, White, Zelano, & Branigan, P.C.

[57] ABSTRACT

A process for the continuous preparation of aniline by hydrogenating nitrobenzene with hydrogen is disclosed which comprises the steps of suspending, in an aniline solvent, a catalyst of palladium or palladium-platinum which is deposited on a lipophilic carbon having an oil absorbency of at least 100, and carrying out reaction at a temperature of from 150° to 250° C. substantially in the absence of water while aniline and water formed in said reaction are continuously distilled off as vapor from the reaction product, and the concentration of nitrobenzene in the reaction solution is maintained at 0.01% by weight or less, wherein a zinc compound is added to the reaction system as a promotor and carbon monoxide is added to the hydrogen at a concentration of 1–500 ppm.

12 Claims, No Drawings

PROCESS FOR PREPARING HIGH-PURITY ANILINE

BACKGROUND OF THE INVENTION

1. Field of the Invention

The present invention relates to a process for preparing aniline by hydrogenating nitrobenzene. Aniline is a very important compound as a basic raw material for urethanes, rubber chemicals, dyes, medicines and the like.

2. Description of the Related Art

U.S. Pat. No. 2,292,879 discloses a process in which an aromatic nitro-compound is hydrogenated in a liquid phase to prepare a corresponding aromatic amine. In this process, a catalyst of nickel, cobalt or copper supported on a finely ground carrier is dispersed in the mixture of an aromatic nitro-compound and an aromatic amine which is the hydrogenation product of the nitro-compound. Hydrogen is then passed through the mixture to carry out reaction. The specification of the U.S. patent discloses that the reaction is carried out under conditions of continuously distilling off water formed by the reaction together with the amine from the reaction system, whereby the activity of the catalyst can be maintained at a high level, and that the aromatic amine is used as a reaction solvent in the reaction so as to relatively heighten the concentration of this amine, whereby the activity of the catalyst can be increased.

Japanese Patent Publication No. 50-15779 discloses that in a liquid phase reaction as in the above-mentioned U.S. patent, the concentration of a produced aromatic amine which is used as a solvent is maintained at 95% by weight or more in the liquid phase, and the reaction is carried out under a pressure as close as possible to atmospheric pressure and at the boiling point of the liquid or a temperature close thereto, so that water produced by the reaction can be easily removed from the system and so that the aromatic amine of the product distilled off from the reactor conveniently contains a lower amount of nitro-compound.

Furthermore, in order to inhibit the production of undesirable impurities as by-products, it is suggested in the above-mentioned Japanese Patent Publication No. 50-15779 that an organic base such as alkanolamine be added. For example, in the case of the preparation of aniline by hydrogenation of nitrobenzene, triethanolamine is added but, even in this case, condensed aniline which has been distilled off still contains about 0.02% or less of nitrobenzene and about 0.5% or less of impurities having hydrogenated nuclei. It is further described in the above-mentioned publication that when triethanolamine is not added, a larger amount of impurities is present in the condensed aniline and it is difficult to separate the aniline layer of the condensed aniline product from a water layer. In fact, when the present inventors carried out a tracing test by the use of a diatomaceous earth-nickel catalyst in accordance with the procedure of Example 1 in Japanese Patent Publication No. 50-15779, the condensed aniline which was distilled off contained 0.05% or more of unreacted nitrobenzene and 0.6% or more of compounds having hydrogenated nuclei.

As methods for eliminating these drawbacks, the present inventors have filed two patent applications regarding processes for preparing high-purity aniline. The first process comprises the steps of dispersing, in an aniline solvent, a lipophilic carbon having an oil absorbency of at least 100 on which a catalyst of palladium or palladium-platinum is deposited, and then carrying out the reaction at a temperature of from 150° to 250° C. substantially in the absence of water while the concentration of nitrobenzene in the reaction solution is maintained at 0.5% by weight or less and during which, aniline and water formed in the reaction are continuously distilled out as vapor from the reaction product (Japanese Patent Laid-open No. 57-1679460). The second process for continuously preparing high-purity aniline by the catalytic hydrogenation of nitrobenzene comprises the steps of carrying out the reaction in the presence of a compound selected from the group consisting of alkali metal hydroxides, alkali metal carbonates, alkali metal bicarbonates, zinc acetate and zinc nitrate during which the concentration of nitrobenzene in the aniline reaction solution is maintained at 0.5% by weight or less (Japanese Patent Laid-open No. 58-4750). These methods can provide aniline having a higher purity than the conventional process, but further improvement is desired.

SUMMARY OF THE INVENTION

An object of the present invention is to provide a process for preparing high-purity aniline containing less impurities than the previously suggested two methods and at high productivity.

The present invention involves a process for the continuous preparation of aniline by hydrogenating nitrobenzene with hydrogen by the steps of suspending in an aniline solvent a catalyst of palladium or palladium-platinum deposited on a lipophilic carbon having an oil absorbency of at least 100, and carrying out the reaction at a temperature of from 150° to 250° C. substantially in the absence of water and during which, aniline and water formed in the reaction are continuously distilled off as vapor from the reaction product. The concentration of nitrobenzene in the reaction solution is maintained at 0.01% by weight or less, which process is characterized in that a zinc compound is added to the reaction system as a promotor and carbon monoxide is added to the hydrogen at a concentration of 1–500 ppm.

According to the process of the present invention, the production of substances having hydrogenated nuclei can be inhibited more effectively than the two methods previously suggested by the present inventors, and aniline which is substantially free from unreacted nitrobenzene can be obtained. Thus, high-purity aniline can be prepared with extremely high productivity. Furthermore, aniline prepared by the process of the present invention can be used as a raw material for the manufacture of, for example, methylenedianiline (MDA) without any particular additional purification. High quality MDA can be manufactured without the accumulation of unreacted nitrobenzene in the system of the MDA manufacturing process.

DETAILED DESCRIPTION OF THE INVENTION

In a process for the continuous preparation of aniline by hydrogenating nitrobenzene wherein aniline is used as a solvent, it is desirable to maintain a high-level concentration of an amine in the reaction solution because the content of the unreacted nitro-compound in a product which is distilled off from the reaction system can thereby be lowered. Furthermore, in the case of a reaction involving a large amount of exothermic heat, as in this reaction, it is generally recommended that a large amount of a solvent be used to control the reaction temperature by using the latent heat of the solvent.

For the above reasons, it appears beneficial to maintain the concentration of the amine in the reaction solution at a level as close as possible to 100% and to lower the concentration of the nitro-compound. However, when the reaction is carried out while decreasing the supply of the nitro-compound per unit time so as to lower the concentration of the nitro-compound in the reaction system, the production of the amine per unit time also decreases accordingly, with the result that production efficiency deteriorates. A more important point is that when the concentration of the nitro-compound is lowered in an amine solvent, hydrogenation of an aromatic ring easily occurs as a side reaction, resulting in the easy formation of such impurities as cyclohexylamine, cyclohexanone, cyclohexylideneaniline and cyclohexylaniline. The lower the concentration of the nitro-compound in the reaction system, the higher the ratio of these by-products. Therefore, an excessive drop in the concentration of the nitro-compound in the reaction system leads to the undesirable production of aniline containing increased amount of compounds having hydrogenated nuclei. In order to obtain high-purity aniline meets the standards for commercial products, it is necessary to carry out complex purification steps such as are incorporated in conventional aniline manufacturing processes. Moreover, it has been found that the lower the concentration of the nitro-compound in the reaction system, the more rapid the accumulation of impurities having high boiling points and tar-like substances in the reaction solution with the progress of the reaction. These impurities and tar-like substances lower the activity and shorten the life of the catalyst, and this makes it difficult to perform a long-term continuous reaction which is economical.

As a means of solving these problems and as a technique for improving the process of Japanese Patent Publication No. 50-15779, the present inventors developed the two methods described above.

However, as a result of further investigation by the present inventors, it has been found that the proposed two methods do not achieve the objective of maintaining the quality of distilled aniline at a high level with a nitro-compound concentration of 0.01% by weight or less in the reaction system.

The present invention is directed to a process for preparing aniline by hydrogenating nitrobenzene, and more specifically, it is directed to a process which has been developed by additionally improving the above two methods previously proposed by the present inventors.

The present invention is directed to a process for the continuous preparation of aniline by hydrogenating nitrobenzene with hydrogen which comprises the steps of suspending, in an aniline solvent, a catalyst of palladium or palladium-platinum which is deposited on a lipophilic carbon having an oil absorbency of at least 100, and carrying out the reaction at a temperature of from 150° to 250° C., substantially in the absence of water, and during which the aniline and water formed in the reaction are continuously distilled off as vapor from the reaction product and the concentration of nitrobenzene in the reaction solution is maintained at 0.01% by weight or less, wherein a zinc compound is added to the reaction system as a promotor and carbon monoxide is added to the hydrogen at a concentration of 1–500 ppm.

The catalyst used in the present invention is a palladium or palladium-platinum catalyst deposited on a nonporous lipophilic carbon having an oil absorbency of 100 or more. The oil absorbency of this carrier, as defined in Japanese Patent Publication No. 32-9320, is represented by the number of parts by weight of a raw cotton seed oil having an acid value of from 2 to 4 per 100 parts by weight of carbon which can gel. In general, a commercially available catalyst of palladium and/or platinum which is supported on a porous active carbon or alumina as a carrier cannot provide good results in the present invention. The carrier required in the present invention is a lipophilic carbon having an oil asorbency of 100 or more, preferably in the range of from 150 to 300. Moreover, a suitable carrier has a particle diameter of from 20 to 60 mμ and a surface area of from 50 to 100 m²/g.

The above-mentioned main catalyst can be prepared by the usual process, which comprises precipitating a palladium and/or platinum compound in an aqueous dispersion of the lipophilic carbon carrier, as described in the specification of the previously mentioned Japanese publication No. 32-9320. The concentration of palladium or palladium and platinum deposited on the lipophilic carbon is preferably in the range of from 0.1 to 5% by weight, and more preferably from 0.5 to 1.0% by weight. Palladium may be used alone, but when palladium is used together with platinum, particularly large effects can be obtained in terms of activity and selectivity. In this case, it is desirable that platinum be used in the range of about 5 to 20% by weight with respect to palladium. In addition, as described in the specification of the above-mentioned Japanese publication, the carrier may contain a small amount of an oxide or a hydroxide of a metal such as iron or nickel. The concentration of the catalyst in the reaction mixture is usually from 0.2 to 2.0% by weight.

In the present invention, examples of the zinc compound to be added as promotors include zinc oxide, zinc acetate, zinc oxalate and zinc nitrate.

An amount of zinc compound is added to the reaction system which achieves a concentration of usually from 10 to 500 ppm (in terms of the metal), and preferably from 20 to 200 ppm. When the concentration thereof is lower than this range, no effect can be perceived, and when it is higher than this range, the main reaction for producing aniline from nitrobenzene is disturbed, resulting in an increase of unreacted nitrobenzene.

In the present invention, an additional promotor such as carbonate or bicarbonate of an alkali metal can be used. Examples of carbonates and bicarbonates of alkali metals include lithium carbonate, sodium carbonate, potassium carbonate, rubidium carbonate, sodium bicarbonate, potassium bicarbonate and cesium bicarbonate. Of these, sodium carbonate and sodium bicarbonate are preferable. The effects of these carbonates or bicarbonates are to inhibit the accumulation of by-product having a high melting point in the reaction vessel and to promote the reaction velocity of the main reaction.

Organic bases described in the above-mentioned Japanese Patent Publication No. 50-15779 do not exhibit any effect when used together with the zinc compound.

The amount of the carbonate or bicarbonate of an alkali metal to be added to the reaction system is usually from 10 to 500 ppm (in terms of the metal) and preferably from 20 to 200 ppm. When the amount thereof is over 500 ppm, the main reaction for producing aniline from nitrobenzene is disturbed. The tendency of this disturbance is more noticeable than in the case of the zinc compound.

In the present invention, the amount of carbon monoxide mixed with the hydrogen is 1–500 ppm, preferably 5–200 ppm, and particularly 10–100 ppm. When the amount is less than 1 ppm, no effect can be perceived, and when the amount is more than 500 ppm, the hydrogenation reaction is disturbed, and the amount of unreacted nitrobenzene increases. The amount of carbon monoxide to be added is determined appropriately by considering the amounts of the main catalyst and the promotor.

When the preparation of aniline is carried out by the present invention, the presence of water in the reaction system causes the activity of the catalyst to decrease and by-products to increase. Therefore, the water formed during the reaction must be continuously removed from the reaction system, so that the reaction is effected substantially free from water. Accordingly, in the process of the present invention, the reaction is carried out by introducing a small amount of nitrobenzene into a reactor through one path, and the introduced nitrobenzene is instantaneously converted into aniline and water and the reaction product is removed in a vapor state from the system.

Removal of the reaction product can be achieved by evaporating nearly all the reaction product by using a part the reaction heat generated at a reaction temperature range of from 150° to 250° C. which can be suitably selected in connection with hydrogen pressure. Afterward, the vapor is condensed and water is separated from aniline and then removed from the system. At this time, it is desirable that a part of the aniline condensate be returned to the reactor so that the volume of the solution in the reactor is kept at a substantially constant level during the reaction.

In the present invention, the hydrogenation can be achieved even under atmospheric pressure. However, the performance of the hydrogenation under atmospheric pressure leads to the relative increase of impurities, with the result in a shorter life of the catalyst. Therefore, it is preferred that the hydrogenation be carried out under a pressure of from 1.5 to 10 atm, and preferably from 3 to 7 atm.

The reaction temperature is in the range of from 150° to 250° C. When the temperature is lower than 150° C., the reaction is too slow and the production per hour is low. In addition, in order to effectively remove water formed during the reaction from the system, a temperature of 150° C. or higher is necessary. However, when the temperature is higher than 250° C., the by-products increase.

In the process of the present invention, the reaction is carried out while the aniline solvent is fed with the raw material nitrobenzene in an amount substantially corresponding to nitrobenzene to be converted into aniline so that the concentration of nitrobenzene in the reaction solution may be maintained at 0.01% by weight or less, and preferably 0.005% by weight or less. When the reaction is carried out at nitrobenzene concentrations of more than 0.01% by weight (but less than 0.5% by weight) in the reaction solution, the distilled aniline contains about 50 ppm of nitrobenzene and is colorless or light yellow. If this aniline product is directly used as the raw material for the manufacture of methylenedianiline (MDA), the obtained MDA has a slightly yellowish tint, and if the excess aniline from the manufacture of MDA is recovered and recycled, nitrobenzene tends to accumulate in this recycled aniline. Therefore, if the hydrogenation reaction can be performed while the product is kept in a state of high quality and while the concentration of nitrobenzene in the reaction solution is maintained at 0.01% by weight or less, the productivity of aniline can be improved, the thus obtained aniline can provide MDA having extremely high quality, and it is also possible to prevent nitrobenzene from accumulating in the recycled aniline during the manufacture of MDA. It is fair to say that the above-mentioned concept is industrially advantageous.

The present invention will now be described in more detail in reference to exmaples.

EXAMPLE 1

500 g of aniline, 0.25 g of a hydrogenating catalyst obtained by depositing 0.8% by weight of palladium, 0.1% by weight of platinum and 0.8% by weight of iron on carbon powder having an oil absorbency of 260 and 0.05 g of zinc acetate were placed in a 1-liter stainless steel autoclave equipped with an inlet through which nitrobenzene, the catalyst and a hydrogen gas can be continuously fed, an outlet through which the unreacted hydrogen gas and a product can be removed from a reaction system, a condenser, a stirrer and a thermometer. While the internal temperature and total pressure were maintained at 190°–200° C. and 5 kg/cm$^2$-G, respectively, nitrobenzene, the catalyst, zinc acetate, and hydrogen containing 50 ppm of carbon monoxide were fed at rates of 130 g/hr, 0.033 g/hr, 0.005 g/hr, and 90–110 liters/hr, respectively, and the resulting water and aniline were removed continuously together with the unreacted hydrogen gas in a vapor state from the reaction system. This vapor was then introduced into the condenser connected to the autoclave and cooled therein, whereby water and aniline were condensed. During this operation, the flow rate of the hydrogen gas was adjusted so as to distill off aniline in an amount corresponding to the aniline produced from the feed nitrobenzene, i.e., so as to always maintain the weight of the liquid phase mainly comprising aniline in the autoclave at about 500 g. On the other hand, the solution corresponding to the amounts of the catalyst and zinc acetate fed (approximately 10% by weight of the nitrobenzene fed) was drawn out from the reactor at various times in order to maintain the concentration of the catalyst and zinc acetate at constant levels. The drawn solution was filtered and then analyzed in order to determine the concentration of nitrobenzene and the amounts of substances having hydrogenated nuclei such as N-cyclohexylaniline and the like and other by-products. The resulting condensate was separated into two layers, thereby obtaining a colorless transparent aniline layer. This aniline layer contained about 4.5% of water. According to the analyzed results by means of gas chromatography and polarography, impurities such as cyclohexanol, cyclohexanone, cyclohexylideneaniline and nitrobenzene were present in amounts of less than 10 ppm, 20 ppm, 20 ppm and 5 ppm, respectively, and the purity of the aniline was 99.99% or more. During the reaction, the reaction solution in the reactor was discontinuously analyzed, which confirmed that the concentration of nitrobenzene was kept at 0.01% or less. Therefore, it was not necessary to decrease the feed of nitrobenzene or to increase the feed of the catalyst. In this liquid phase, N-cyclohexylaniline was detected, but its content was only 0.05% after 9 hours had elapsed from the start of the reaction.

EXAMPLE 2

The reaction was carried out using the same apparatus and the same procedure as in Example 1 except that a concentration of carbon monoxide of 100 ppm in hydrogen was used. In this case, the distilled aniline layer contained impurities of 10 ppm or less of cyclohexanol, 50 ppm or less of cyclohexanone, 20 ppm or less of cyclohexylideneaniline and 5 ppm or less of nitrobenzene, and the purity of the aniline was 99.99% or more. Furthermore, during the reaction, the concentration of nitrobenzene in the liquid phase in the reactor was kept at 0.01% or less, and the content of N-cyclohexylaniline was only 0.06% after 9 hours had elapsed from the start of the reaction. Therefore, it was not necessary to decrease the feed of nitrobenzene and/or increase the feed of the catalyst.

COMPARATIVE EXAMPLE 1

The reaction was carried out using the same apparatus and the same procedure as in Example 1 except that zinc acetate was not employed. In this case, the distilled aniline layer contained as impurities of 200–400 ppm of cyclohexanol, 1300–2200 ppm of cyclohexanone, 80–150 ppm of cyclohexylideneaniline and 20 ppm of nitrobenzene, and the purity of the aniline was only 99.68–99.80%. Furthermore, in the liquid phase in the reactor, N-cyclohexylaniline was formed rapidly and its content reached about 1.7% after 9 hours had elapsed from the start of the reaction, although the content of nitrobenzene in this liquid phase was maintained at 0.01% or less.

EXAMPLES 3 TO 6 AND COMPARATIVE EXAMPLES 2 AND 3

The same procedure as in Example 1 was employed except that the kinds and amounts of promotors and the contents of carbon monoxide in hydrogen were changed. The results are set forth in Table 1.

2. The process of claim 1, wherein the concentration of palladium or palladium-platinum alloy on the carbon is from 0.5 to 1%.

3. The process of claim 1, wherein the catalyst is a palladium-platinum alloy containing about 5 to 20% palladium.

4. The process of claim 1, wherein the concentration of catalyst in the reaction mixture is from 0.2 to 2% by weight.

5. The process of claim 1, wherein the concentration of the zinc compound in the reaction mixture is from 20 to 200 ppm.

6. The process of claim 1, wherein the zinc compound is zinc oxide.

7. The process of claim 1, wherein the zinc compound is zinc acetate.

8. The process of claim 1, wherein continuous streams of the nitrobenzene, catalyst, zinc promoter and hydrogen are introduced into a reaction zone heated at 150° to 250° C. and containing aniline, catalyst and zinc compound and continuous streams of aniline, water and unreacted hydrogen are removed from the reaction zone.

9. The process of claim 1, wherein the catalyst is a palladium-platinum alloy containing about 5 to 20% palladium and the concentration thereof on the carbon is from 0.5 to 1%; wherein the concentration of catalyst in the reaction mixture is from 0.2 to 2% by weight; wherein the concen-

TABLE 1

| | Content of CO in Hydrogen (ppm) | Promotor | | | | Reaction Pressure $kg/cm^2$-G | Impurities in Distilled Aniline (ppm) | | | |
|---|---|---|---|---|---|---|---|---|---|---|
| | | Zinc Compound | | Alkali Metal Bicarbonate | | | | | | |
| | | Kind | Amount (g) | Kind | Amount (g) | | Cyclo-hexanol | Cyclo-hexanone | Cyclohexyl-ideneaniline | Nitro-benzene |
| Example 3 | 50 | zinc acetate | 0.06 | — | — | 5 | <10 | <30 | <20 | <5 |
| Example 4 | 50 | zinc nitrate | 0.05 | NaHCO$_3$ | 0.1 | 5 | <10 | <50 | <20 | <5 |
| Example 5 | 100 | zinc oxide | 0.07 | — | — | 6 | <10 | <20 | <20 | <10 |
| Example 6 | 180 | zinc acetate | 0.10 | — | — | 6 | <10 | <20 | <20 | <10 |
| Comp. Ex. 2 | 0 | zinc acetate | 0.08 | — | — | 5 | <200 | <1000 | <100 | <20 |
| Comp. Ex. 3 | 500 | zinc acetate | 0.06 | — | — | 6 | <10 | <20 | <20 | <100 |

What is claimed is:

1. A process for the continuous preparation of aniline wherein nitrobenzene is hydrogenated with hydrogen in an aniline solvent containing suspended therein a catalyst of palladium or palladium-platinum which is deposited on a lipophilic carbon having an oil absorbency of at least 100, at a temperature of from 150° to 250° C. substantially in the absence of water while aniline and water formed in said reaction are continuously distilled off as vapor from the reaction product, and the concentration of nitrobenzene in the reaction solution is maintained at 0.01% by weight or less, which comprises adding a zinc compound selected from the group consisting of zinc oxide, zinc acetate, zinc oxalate and zinc nitrate to the reaction system as a promoter and adding carbon monoxide to the hydrogen at a concentration of 5–200 ppm.

tration of the zinc compound in the reaction mixture is from 20 to 200 ppm; and wherein the zinc promoter is zinc oxide.

10. The process of claim 9, wherein the zinc promoter is zinc acetate.

11. The process of claim 8, wherein the catalyst is a palladium-platinum alloy containing about 5 to 20% palladium and the concentration thereof on the carbon is from 0.5 to 1%; wherein the concentration of catalyst in the reaction mixture is from 0.2 to 2% by weight; wherein the zinc compound is zinc oxide and the concentration thereof in the reaction mixture is from 20 to 200 ppm.

12. The process of claim 11, wherein the zinc promoter is zinc acetate.

* * * * *